United States Patent [19]
Moreno et al.

[11] Patent Number: 5,908,786
[45] Date of Patent: Jun. 1, 1999

[54] BLOOD COAGULATION MONITORING DEVICE WITH LIQUID CRYSTAL AND GRADIENT HEATER

[75] Inventors: Mario Moreno, Raleigh; Jogin R. Wu, Durham, both of N.C.

[73] Assignee: Akzo Nobel, N.V., Arnhem, Netherlands

[21] Appl. No.: 08/989,561

[22] Filed: Dec. 12, 1997

[51] Int. Cl.$^6$ .................................................. G01N 33/86
[52] U.S. Cl. ........................... 436/69; 436/164; 436/165; 436/177; 436/178; 422/55; 422/58; 422/73; 422/101; 422/102; 73/64.41; 73/64.43
[58] Field of Search ................................ 436/63, 69, 164, 436/165, 175, 177, 178; 422/55, 58, 73, 101, 102; 73/64.41, 64.43

[56] References Cited

U.S. PATENT DOCUMENTS

| | | | |
|---|---|---|---|
| 4,849,340 | 7/1989 | Oberhardt | 435/13 |
| 4,963,498 | 10/1990 | Hillman et al. | 436/69 |
| 5,058,999 | 10/1991 | Davis | 349/197 |
| 5,135,549 | 8/1992 | Phillips et al. | 95/8 |
| 5,140,161 | 8/1992 | Hillman et al. | 436/69 X |
| 5,144,139 | 9/1992 | Hillman et al. | 250/341.3 |
| 5,164,598 | 11/1992 | Hillman et al. | 250/341.3 |
| 5,204,525 | 4/1993 | Hillman et al. | 250/252.1 |
| 5,300,779 | 4/1994 | Hillman et al. | 436/69 X |
| 5,302,348 | 4/1994 | Cusak et al. | 422/73 |
| 5,372,946 | 12/1994 | Cusak et al. | 436/69 |
| 5,534,226 | 7/1996 | Gavin et al. | 422/73 |
| 5,678,566 | 10/1997 | Dribbon | 600/592 |

OTHER PUBLICATIONS

Derwent Abstract 03321731, M. Parsley, 1991.
Derwent Abstract 011636189, Univ Guizhou, 1996.
D. Burgess et al., *IEEE/IRPS*, 1/84/0119, 1984.
E. M. Fleuren, *IEEE/IRPS*, 5/83/0148, 1983.

*Primary Examiner*—Maureen M. Wallenhorst
*Attorney, Agent, or Firm*—Gregory R. Muir

[57] ABSTRACT

A device and method are disclosed for determining whether or not an individual's blood coagulation time is in a normal or abnormal range, and is particularly suitable for measuring prothrombin time and activated partial thromboplastin time coagulation values. The device includes a housing with an area for receiving a sample, a capillary channel or elongated area with an absorbent material, and a gradient heater. Liquid crystal and a coagulation agent can be disposed within the device to mix with a sample added to the device. The mixture passes along the capillary channel or absorbent material and stops moving when the sample has clotted. Due to the gradient heater and liquid crystal, the mixture may or may not change color, depending upon whether the individual has a an abnormally short, normal, or abnormally long clot time.

23 Claims, 12 Drawing Sheets

BLOOD COAGULATION MONITORING DEVICE WITH LIQUID CRYSTAL AND GRADIENT HEATER

BACKGROUND OF THE INVENTION

The invention relates to measuring whether blood coagulation times are in a normal range or not, and more particularly for measuring PT (prothrombin time) and aPTT (activated partial thromboplastin time) coagulation values to produce qualitative or quantitative results. The invention is a lightweight, portable, disposable device which can give immediate results at a hospital patient's bedside, or can be used for patient self-monitoring in a home setting.

Current trends in the diagnostics industry are full laboratory automation, and point-of-care testing. Full laboratory automation for thrombosis/hemostasis is exemplified by the MDA-180 (Organon Teknika, Durham, N.C.) where, e.g., samples from patients all over a hospital are delivered to a central location where the automated apparatus is located. Patients' blood samples are placed into the machine, after which a variety of assays are performed and results reported. The results are then sent/transmitted back to the area where the patient is located for interpretation by the doctor.

Point-of care testing, on the other hand, though complementary to full laboratory automation, involves smaller devices, often handheld devices with disposable components, which can give results at the patient's bedside (or at home, if the device is for home use). In point-of-care testing, rather than sending a blood sample to a central location for testing, a sample of blood can be placed in a small device at the patient's bedside (or at a location near the patient) so that a test result can be available more quickly. This savings in time can be crucial when the point-of-care testing is for a thrombotic or hemophiliac condition.

In the long run, the trend is for testing devices to become more simple, more portable and more flexible in use. In the coagulation field, rapid technology-driven change is transforming the market for products used in monitoring the coagulation status in heart patients and others treated with anti-coagulant therapy. Also, with managed healthcare resulting in shorter hospital stays, the desirability increases for testing that does not require the use of the central laboratory, and for devices that can be used at home, thus allowing patients to be discharged from the hospital more quickly.

Furthermore, with regard to point-of-care testing in a home setting, studies have shown that self testing can improve patient treatment when compared to the lack of self monitoring of coagulation therapy. Numerous studies have indicated that more frequent PT testing increases the effectiveness and safety of anticoagulant therapy. Effectiveness is measured by a low incidence of thromboemboli, that is, blood clots which can result when the therapeutic dosage is too low. Safety is measured by few or no bleeding incidents, which can occur when the therapeutic dose is too large. With self testing at home, the therapeutic dosage can more easily be kept within a safe range thus improving the treatment of the individual undergoing anticoagulant therapy.

SUMMARY OF THE INVENTION

It is an object of the present invention to provide a lightweight, easy-to-use, portable point-of-care device.

It is a further object of the present invention to provide a point-of-care device for monitoring of hemophiliac or thrombotic conditions, and/or for monitoring of anticoagulant therapy.

It is another object of the present invention to provide a point-of-care device for thrombosis/hemostasis which allows for qualitative results through easy-to-read color discrimination by the user, thus eliminating the need for complex and expensive instrumentation.

It is still a further object of the present invention to provide a point-of-care device which comprises a disposable strip as a housing for an asymmetric membrane, a dry reagent, a thermochromic liquid crystal, and a gradual micro-heater.

The above and other objects of the invention are achieved by the provision of a convenient, easy-to-use, portable point-of-care device which is made of two main components: a) a disposable strip with reagent, liquid crystal and micro-heater, and b) a strip controller which, among other things, controls the micro-heater in the disposable strip. The disposable strip and the strip controller, together form a point-of-care device capable of producing a result indicating normality/abnormality of a patient's coagulation (e.g. PT, aPTT) time.

Various other features and advantages of the invention will become apparent from the detailed description below taken in conjunction with the accompanying drawings and the appended claims.

DETAILED DESCRIPTION OF THE PREFERRED EMBODIMENT

Figure 1:
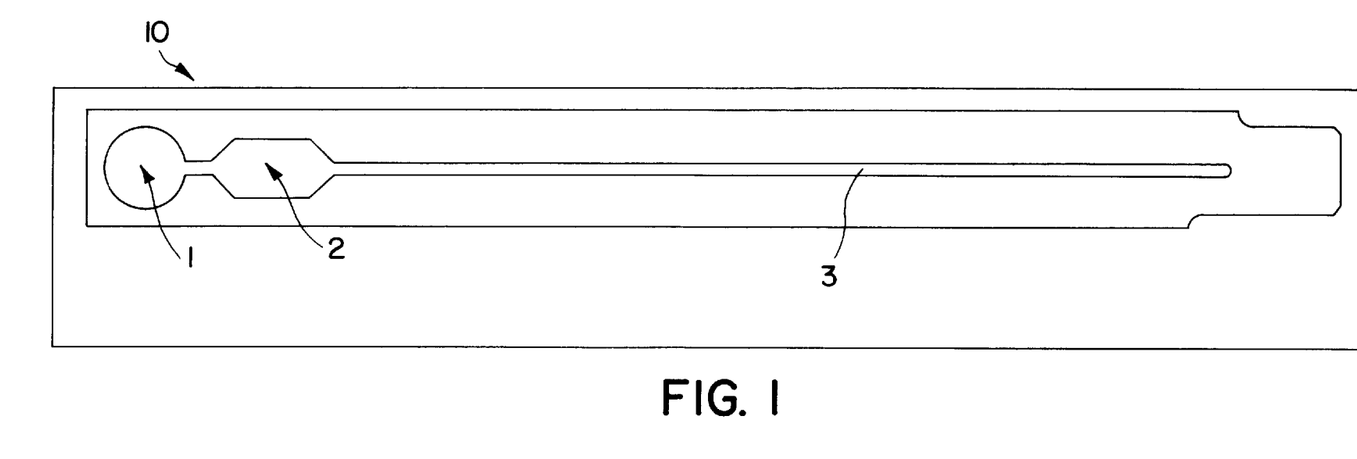
FIGS. 1 and 2 are illustrations of elements of the capillary channel of the invention.

As can be seen in FIG. 1, a sample cavity 1 is formed within housing 10, which cavity is for receiving a sample, such as a blood sample. Sample cavity 1 is in fluid communication with reagent chamber 2, which holds a reagent for reacting with at least one component in the sample being tested. Reagent chamber 2 is in fluid communication with capillary channel 3. As can also be seen in FIG. 2, a capillary channel seal 4 is provided for containing fluid sample within sample cavity 1, reagent chamber 2, and capillary channel 3. The term "capillary channel" is used to denote an area of the device where the sample is pushed or pulled along a length of the device, which could include an area where the sample flows due to gravity, or an absorbent material through which the sample flows.

Figure 2:
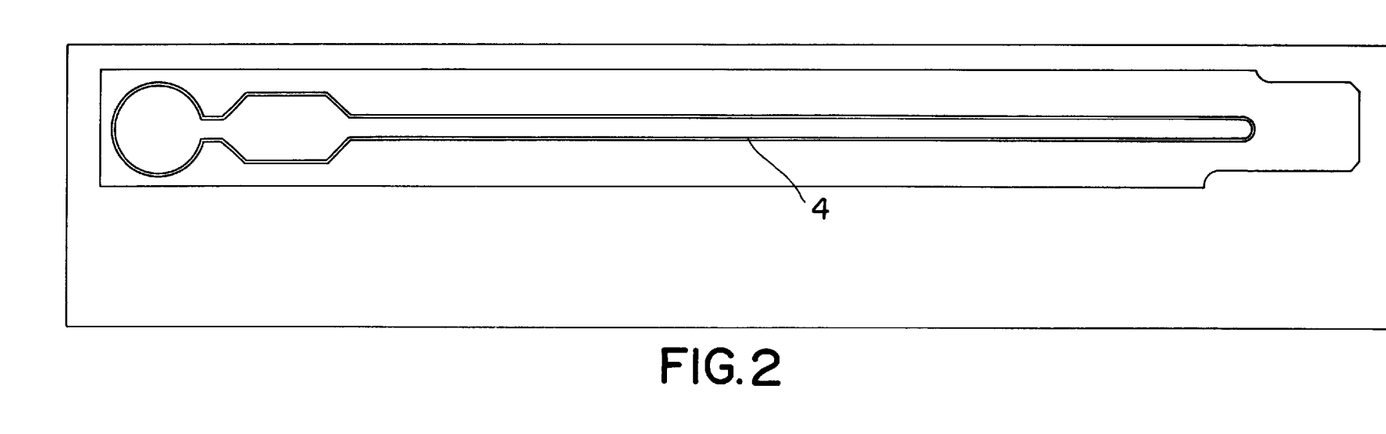
Figure 3:
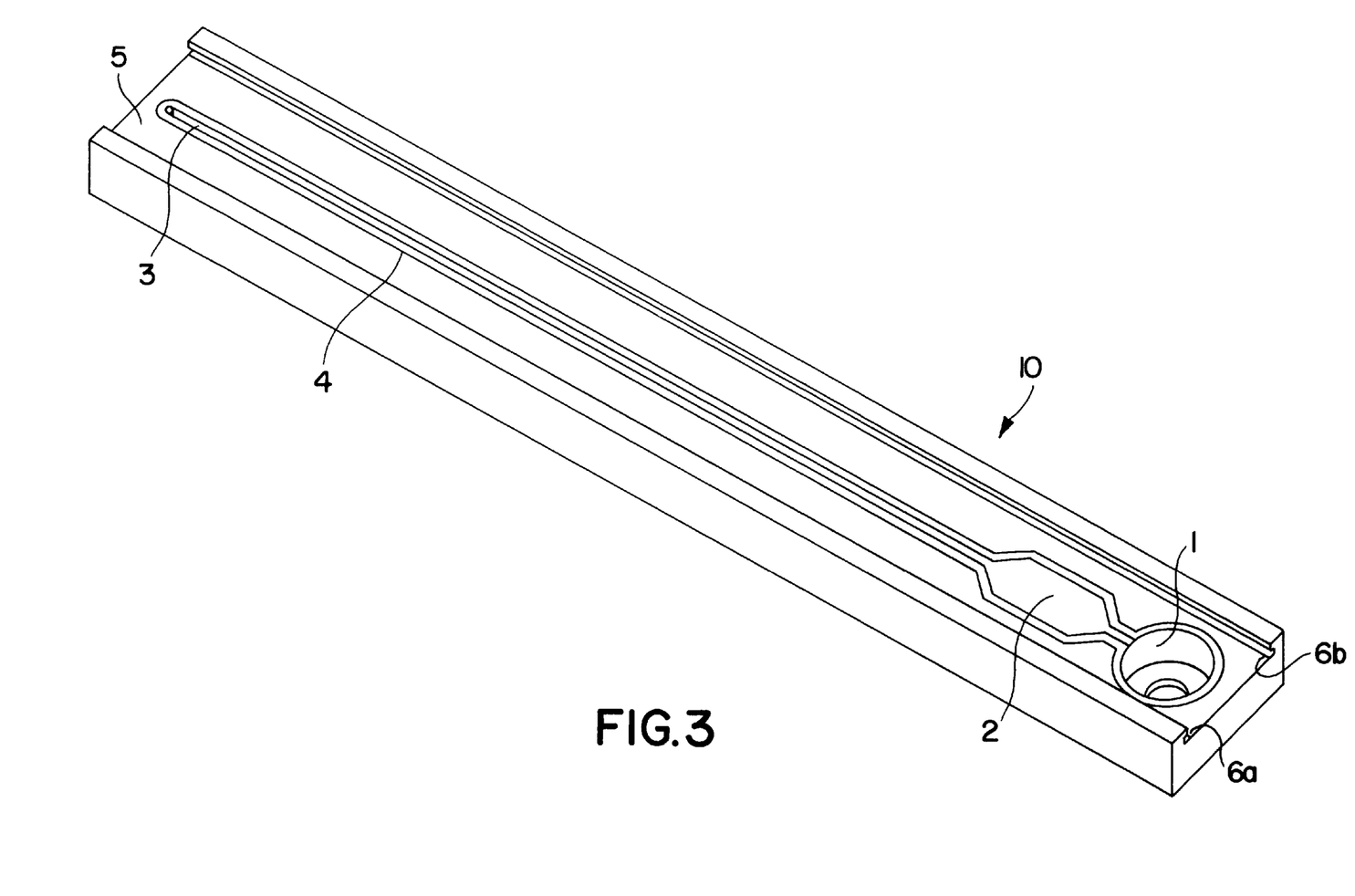
FIG. 3 is an illustration of the housing portion of the invention which includes the capillary channel.

FIG. 3 is an illustration of the housing portion 10 of the point-of-care device. FIG. 3 is an illustration of the bottom of the device, without the micro-heater portion of the device in place. As in FIGS. 1 and 2, there can be seen a sample cavity 1, a reagent chamber 2, and a capillary channel 3. Capillary channel seal 4 extends at least slightly above housing surface 5 so as to create a hermetic seal when the micro-heater portion of the device (not shown in FIG. 3) is in place against the housing surface 5. The micro-heater portion of the device is inserted and held in place by slots 6a and 6b.

Figure 4:
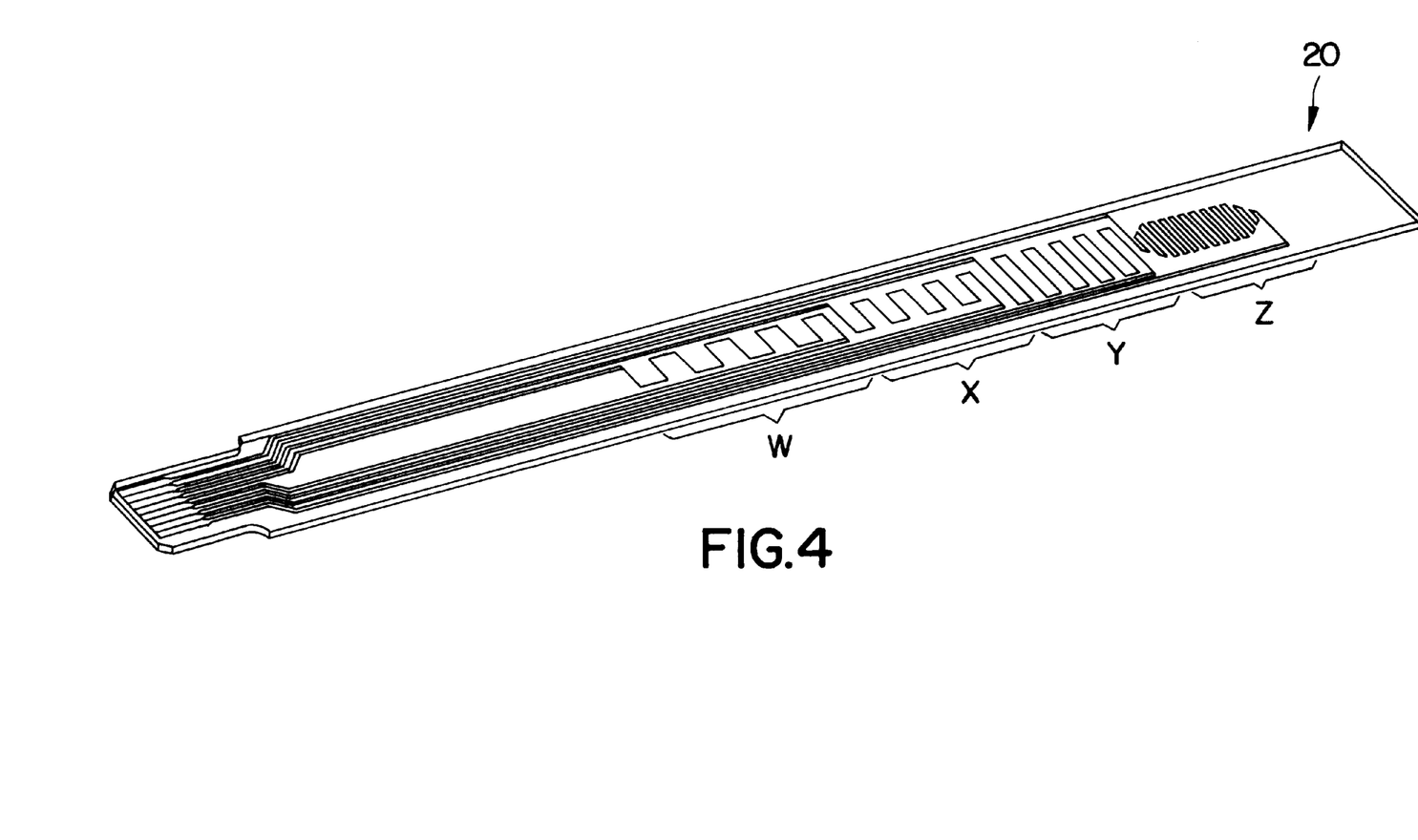
FIGS. 4 and 5 are views of the micro-heater portion of the invention.
Figure 5:
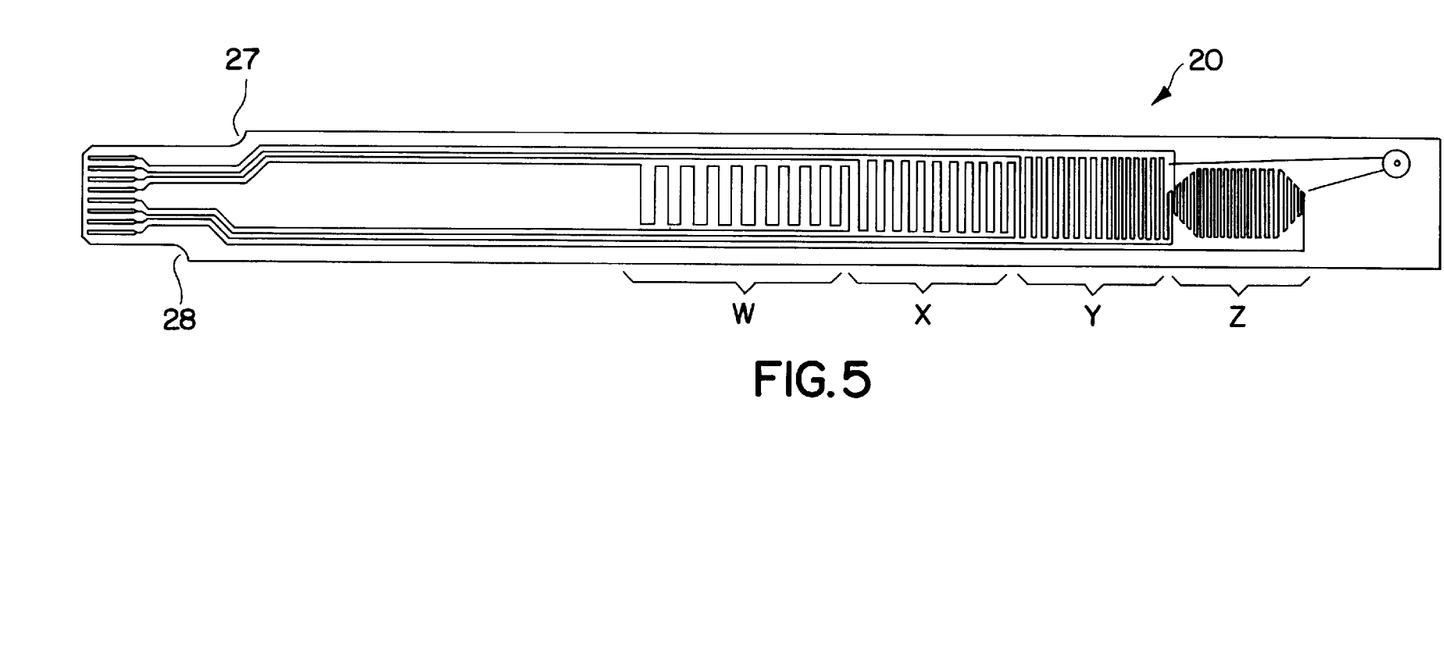

FIGS. 4 and 5 are illustrations of the micro-heater portion of the point-of-care device. As can be seen in these figures, a disposable slide 20 has embedded therein or thereon, a micro-heater element. The micro-heater element can be applied to the slide with printed circuit board techniques. Though the micro-heater could be formed as a single element which changes in density over the length of the slide, the micro-heater can also be formed as illustrated in FIGS. 4 and 5, where multiple sections are provided. As can be seen in these figures, sections W, X, Y and Z are provided with a decreasing density of conductive material from Z to W (section Z having the highest density and which will be disposed below the reagent chamber of the housing).

The temperature gradient along the slide is accomplished in two ways: (1) the intrinsic difference in heater density as mentioned above, and, (2) by different pulse-width-modulation applied to each independent section. The nature of this arrangement is such that if all heater sections are wired in series, the resulting temperature along the slide exhibits a natural gradient. In one embodiment, the closed loop control system could use each heating element also as a feedback sensor (while controlling any one of the elements, the control system uses the resistive value of the others as a thermal reference). This system can also be used in an open loop configuration and controlled by constant current techniques.

Figure 6:
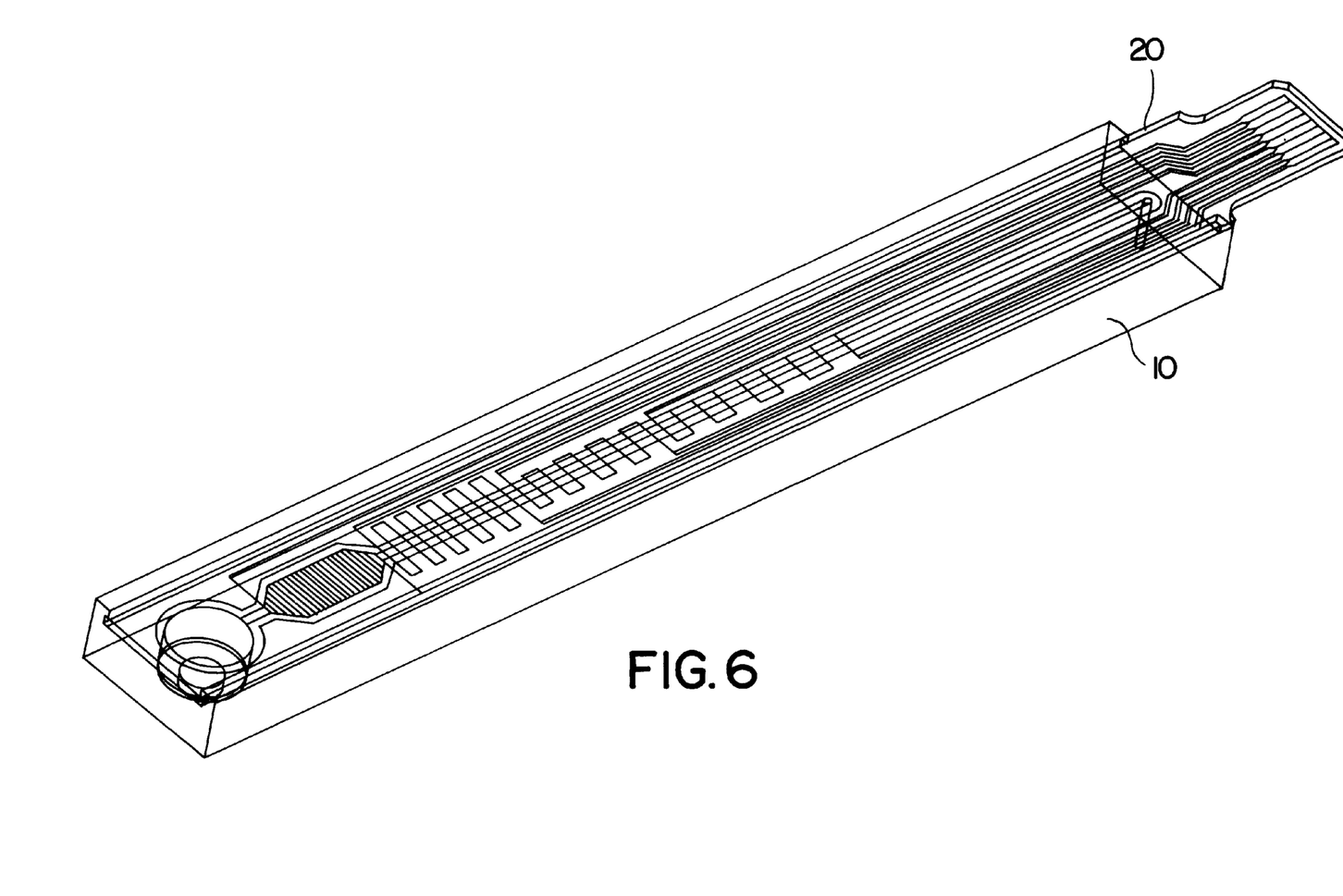
FIG. 6 is a transparent view of the housing portion and the micro-heater portion of the invention fitted together.
Figure 7:
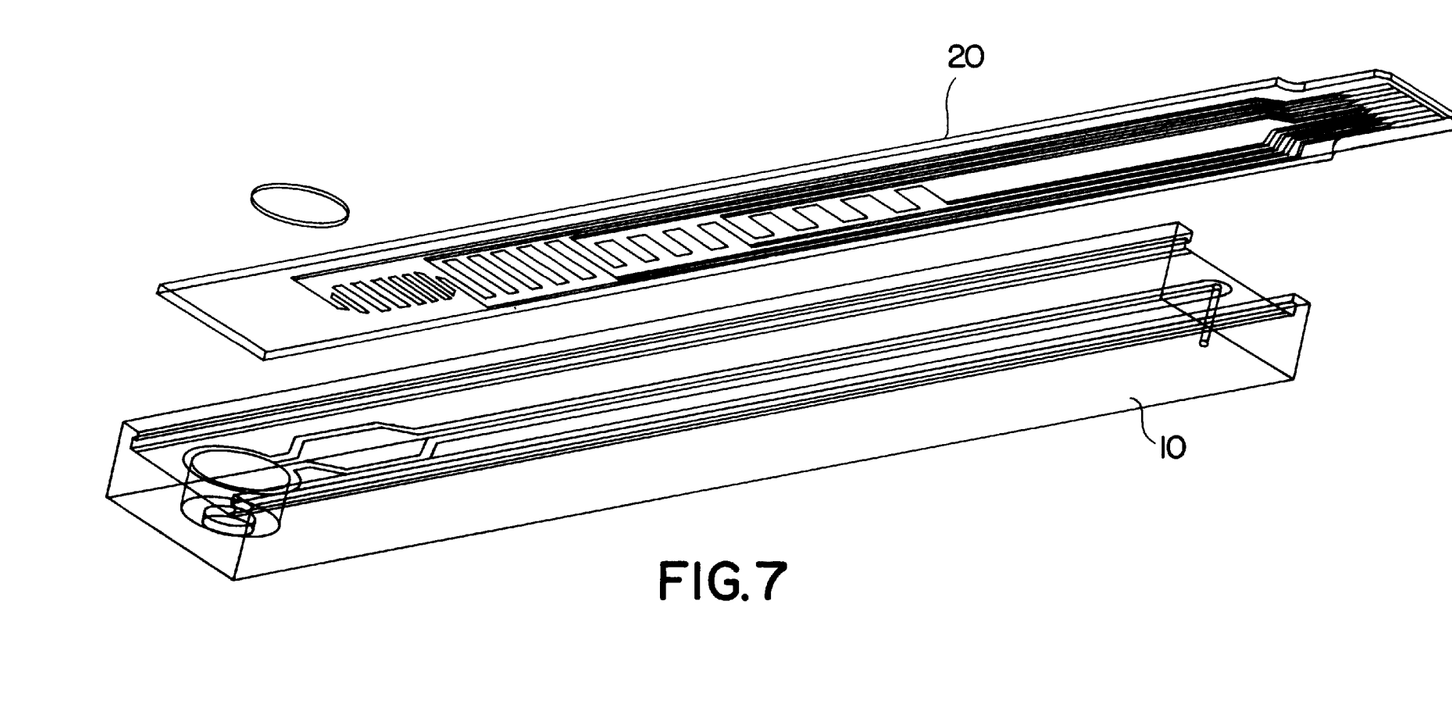
FIG. 7 is an exploded view of the housing portion and the micro-heater portion of the invention.

FIG. 6 is a transparent view and FIG. 7 is an exploded view of the point-of-care device showing both the micro-heater portion 20 and the housing portion 10 of the device together. Also illustrated in FIG. 7 is the symmetric membrane filter disc 24 which fits at the bottom of the sample well in contact with the heater's printed circuit board.

Figure 8A:
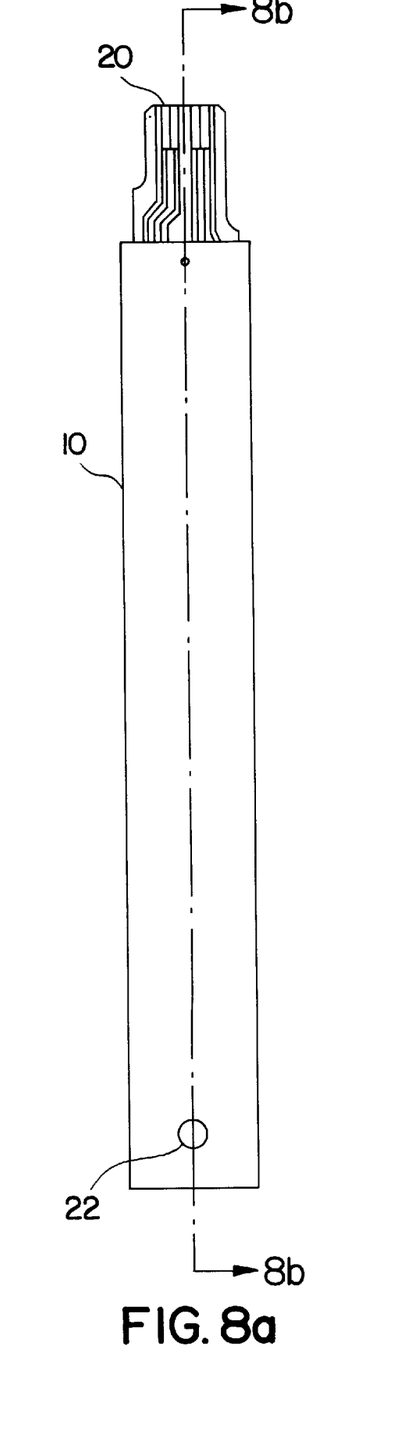
FIGS. 8a and 8b are top and side views, respectively, of the invention.
Figure 8B:
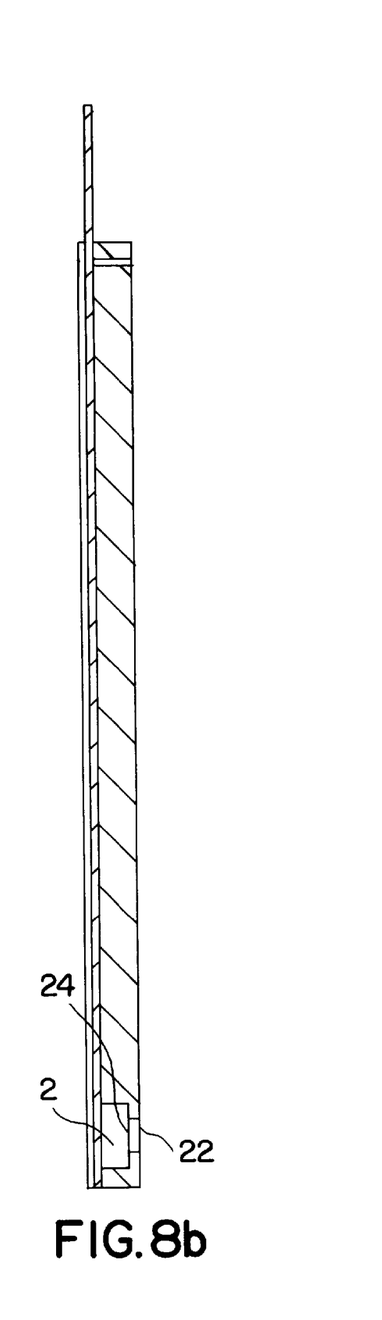

FIG. 8a is a top view of the device where the micro-heater portion of the device is covered by the housing portion, except for the mating end of the micro-heater portion, which mates with a heating controller (not shown in FIG. 8a). Opening 22 in FIG. 8a is for the addition of the fluid sample to be tested into the device. As can also be seen in FIG. 8b, a membrane (e.g. an asymmetrical membrane) 24 is disposed between aperture 22 and sample cavity 1. One example of a suitable membrane is one by MemTec (an asymmetric polysulfone membrane) with a 30 micrometer pore size on one side, and a 3 micrometer pore size on the other. The membrane acts to allow plasma to flow through, if the sample is a whole blood sample, while restricting other parts of the blood sample such as red blood cells.

Figure 9:
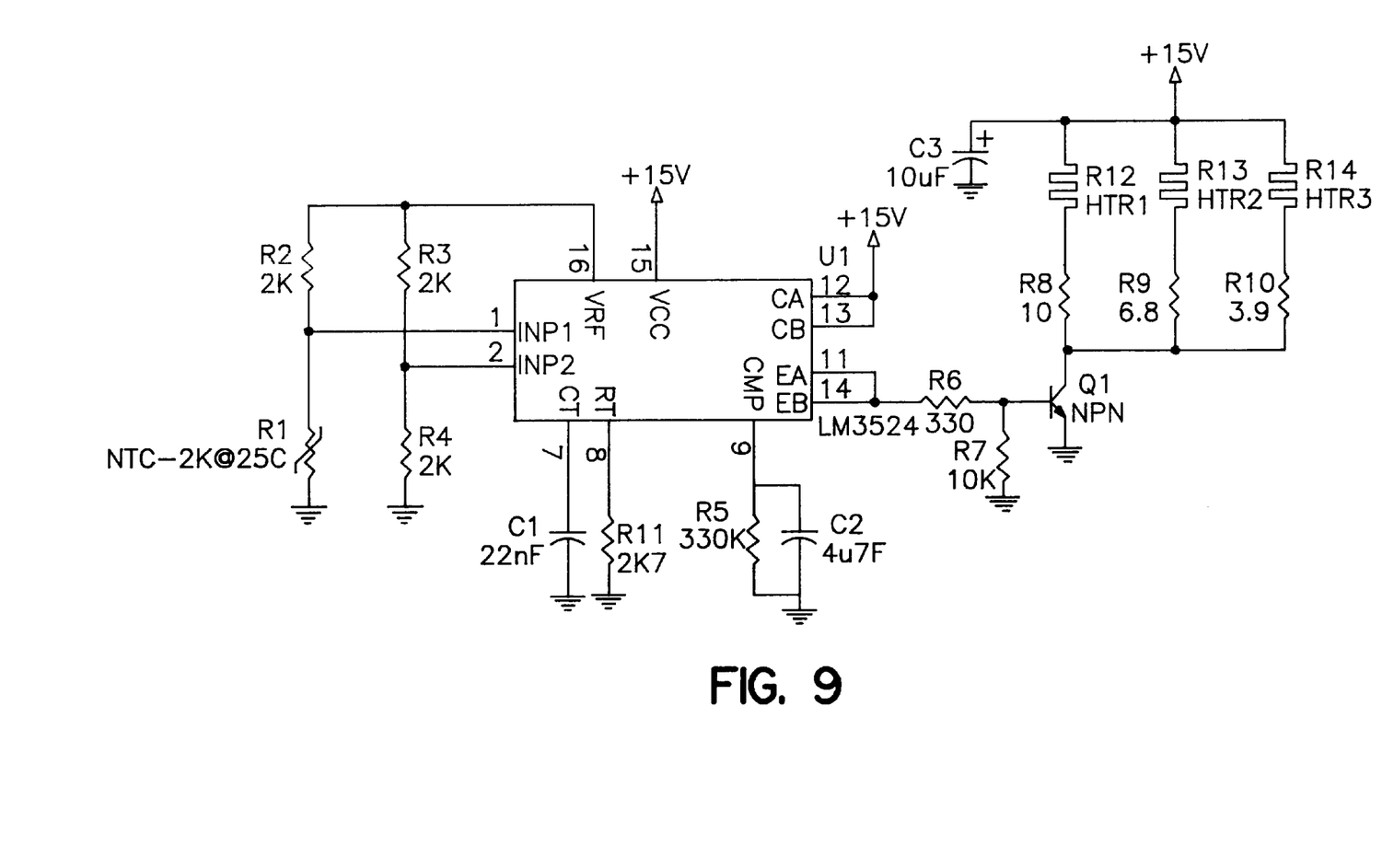
FIG. 9 is a circuit diagram of one embodiment of the heater control of the invention.

FIG. 9 is a circuit diagram of one possible electronic controller of the point-of-care device. The circuit illustrated in FIG. 9 uses an LM3524 PWM IC and an RTD (positive temperature coefficient platinum sensor) as its feedback element. The RTD forms part of a resistive bridge made of 2K ohm resistors. When power is applied, the RD is at its low value, and the LM3524 positive input is at higher potential than the negative input. This forces the LM3524 output to go high, turning the NPN transistor on, driving the heater. When the servo point is reached, the duty cycle of the output signal is reduced from 90% (full on) to whatever value is required to keep the heaters at the correct temperature. Of course, this is but one example of many that could be used to heat the micro-heater element.

The different gradual temperature profile on the flow channel, is accomplished by each section heater which receives a different amount of current due to the limiting series resistors R8, R9, and R10. A smooth temperature transition occurs because of the natural strip dissipation.

Figure 10:
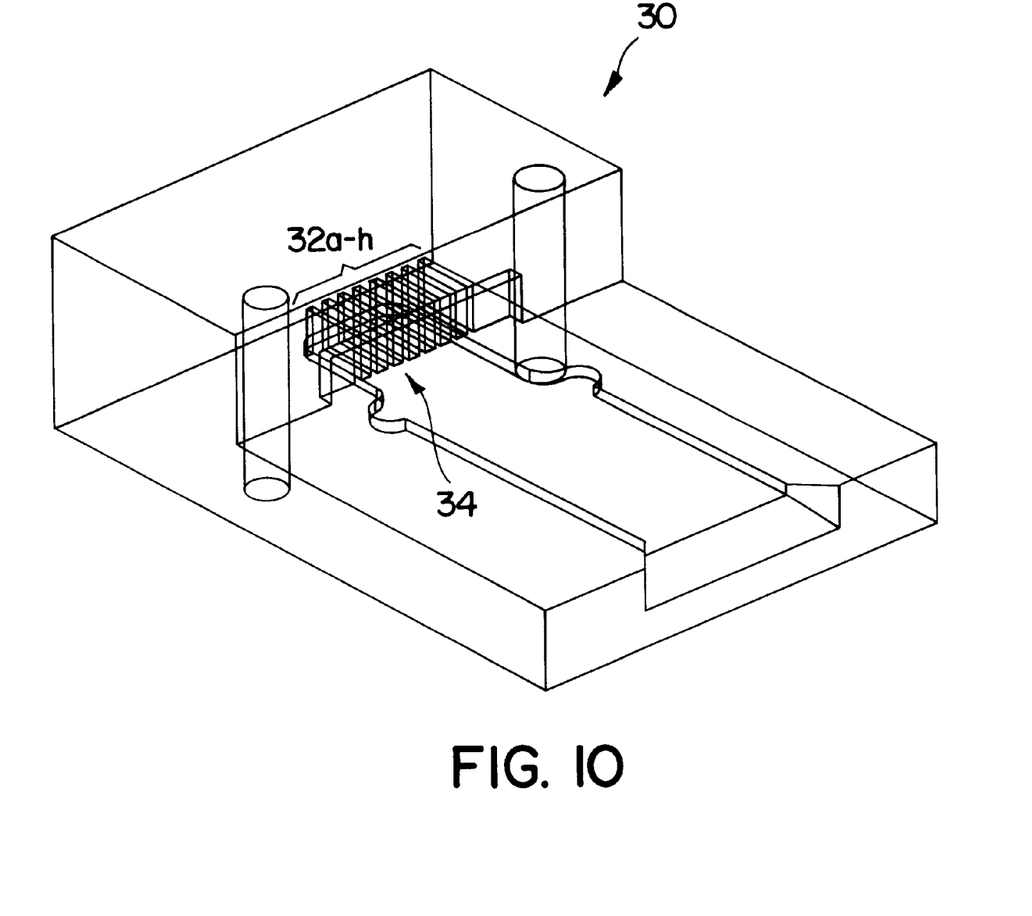
FIG. 10 is an illustration of the interface port for locking with the housing and micro-heater.

As can be seen in FIG. 10, there is illustrated an isometric view of the interface port 30 of the invention. The interface port resembles a modular telephone jack with spring-loaded contacts that will make the connection with the housing/micro-heater assembly. Contacts 32a through 32h each contact a corresponding contact on the micro-heater. The housing/micro-heater assembly slips into slot 34 so as to become engaged with the interface port. The interface port can be equipped with a device that only allows the housing/micro-heater assembly to be inserted in the proper orientation. Or, conversely, the micro-heater itself can be designed so as to fit in only the proper orientation within the interface port. For example, as can be seen in FIG. 5, shoulders 27 and 28 are at different distances from the contact end of the micro-heater. If corresponding shoulders or pins are in place in the interface port, then the proper orientation of the micro-heater into the interface port can be assured.

In order to use the point-of-care device, a fluid sample is obtained. If the fluid sample is a blood sample, it can be obtained by traditional means such as venipuncture or a finger prick. The fluid sample is applied via opening 22 onto membrane 24. Assuming the sample is a blood sample, plasma passes through the membrane so as to be separated from the whole blood and passes through sample cavity 1 into reagent chamber 2. In the reagent chamber, the plasma mixes with the appropriate reagent for the test (if the test is a PT test, then the reagent could be thromboplastin; if the test is an aPTT test, the reagent could be Platelin-L. The reagent is preferably a dry reagent.

The plasma sample also mixes in the reagent chamber with liquid crystal, preferably thermochromic liquid crystal. The reagent chamber comprises two compartments, one compartment having therein the liquid crystal, and the other compartment having the blood clotting reagent, wherein the blood sample passes into and mixes with the liquid crystal and blood clotting reagent in each compartment before passing into the capillary channel. Thermochromic liquid crystal can comprise more than one type of liquid crystal and can be based on two basic materials: 1) cholesteric (comprised of cholesterol or other sterol-related chemicals, and 2) chiralnemetic (non-sterol related). There are two categories within either of the above-mentioned basic materials: 1) transitional temperature bicolor (where a set threshold temperature will determine a single color change, and where further temperature changes below and above the threshold point will not cause other color changes), and 2) continuous temperature range multi-color (where a range of temperatures will show a continuous range of colors -play bandwidth-). In any of the above-mentioned categories, the temperature threshold or range can be set for any one of the possible materials.

The percentage of liquid crystal used is a percentage in relation to the total sample volume. The percentage of liquid crystal should be from 0.001 to 25%, preferably from 0.01 to 2%, and most preferably around 0.05%.

It should be noted that the following test results are considered normal: for a PT test, a value between 10.8 seconds and 12.6 seconds is normal; for an aPTT test, a value between 25 seconds and 38 seconds is normal. Any other value will fall into an abnormal range. Note that smaller values are not clinically significant for coagulation testing. Most abnormal coagulation times will be in larger values (typically indicating Factor deficiencies). The actual lengths on the device can be redefined at any time by the thermal profile and the final device configuration.

EXAMPLE 1

Figure 11:
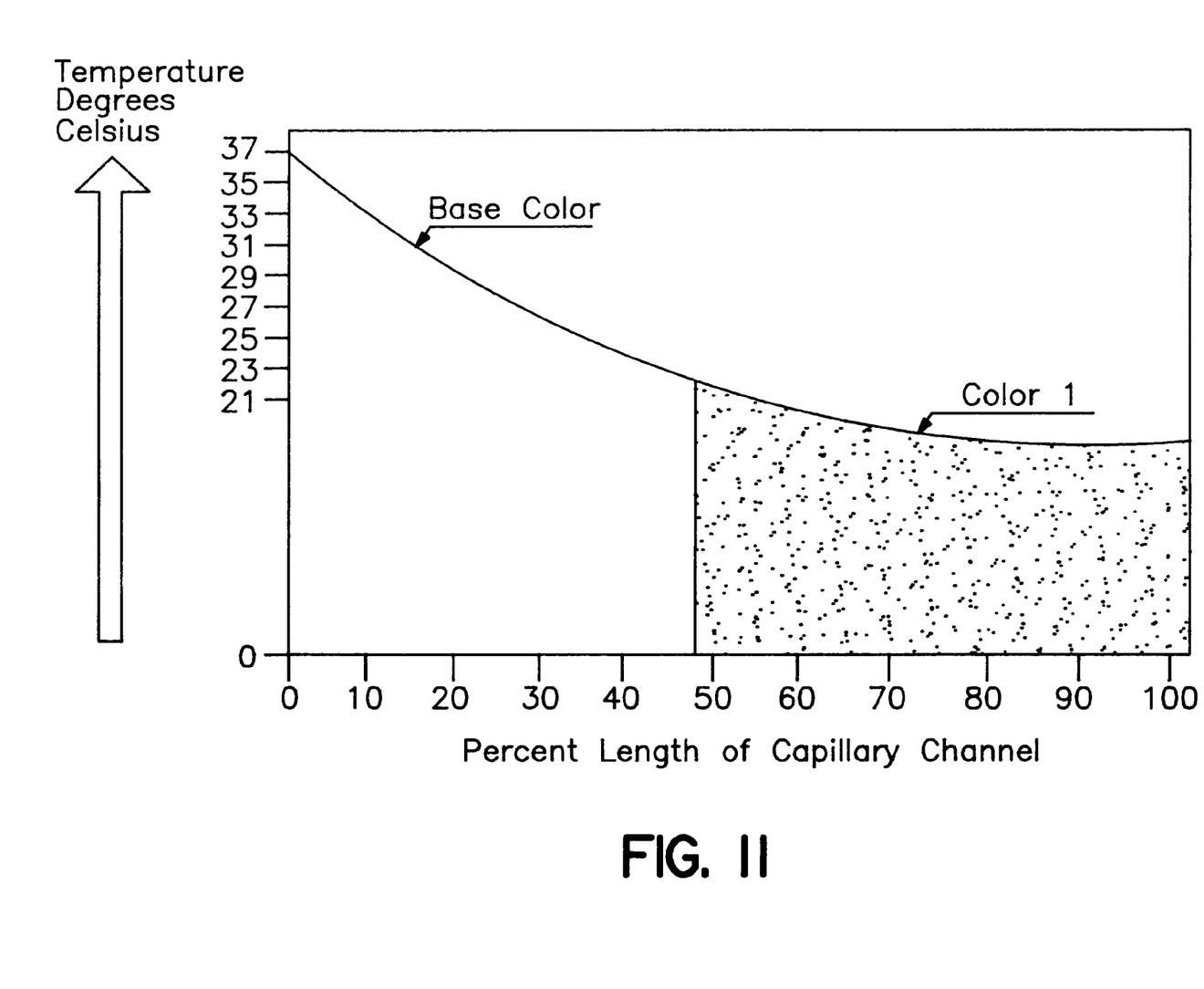
FIG. 11 is a graph showing the change from base color to second color ("color 1") when the temperature goes below a particular value.

After mixing with the reagent and the liquid crystal in the reagent chamber, the mixture passes into the capillary channel and stops at a point in the capillary channel when clot formation has occurred. The device is heated to 37 degrees C. at the reagent chamber, which temperature gradually decreases to below 22 degrees C. at a particular point along the capillary channel. This point is chosen based on what is the maximum length of time that a normal blood sample clots. The liquid crystal is yellow at temperatures above 22 degrees C. Therefore, if the plasma clots and stops travelling along the capillary channel prior to the point where the temperature decreases to 22 degrees C. or below, then the plasma sample will remain yellow along the length of the capillary channel. However, if the plasma fails to clot within a normal period of time, then the mixture of plasma, reagent and liquid crystal will travel past the point at which the temperature drops to below 22 degrees C., such that the liquid crystal will turn red from this point on along the capillary channel. This red color is an indication of a blood clot time abnormality, which can, in a hospital setting, indicate the need for additional tests/treatment, or, in a home setting, indicate the need for the patient to return to his/her physician for additional care. Such a change of color at 22 degrees C. is illustrated in FIG. 11.

EXAMPLE 2

The above example is given in relation to detecting an abnormally long clot time. However, the invention can also be used to detect an abnormally short clot time, or both. The micro-heater, in such an example, would be modified so that the point at which the temperature reaches 22 degrees C. and below, would be set at the minimum normal clot time. In this situation, a patient or his care provider would look for the plasma/reagent/liquid crystal mixture to turn red as an indication of normality. Or, the micro-heater gradient could be reversed to that the temperature increases along the length of the capillary channel from the reagent chamber, with the temperature of 22 degrees still being at the point of the minimum normal clot time. In this way, as in the first example, the mixture will be red in the abnormal range, and fail to turn yellow so as to indicate a blood clot time in a normal range (the patient/doctor would look to make sure that the mixture turns yellow at some point along the capillary channel.

EXAMPLE 3

The micro-heater gradient could also be modified so as to decrease in density so that the temperature drops from 37 degrees C. to 22 degrees C. at a first color-change point corresponding to a minimum abnormal clot time. The micro-heater gradient would be sparse enough for a particular length along the capillary channel so that the temperature is maintained at or below 22 degrees C. along this section. However at a second color-change point along the capillary channel, the density of the micro-heater is sufficient to bring the temperature back up past 22 degrees C. This second color-change point is set so as to correspond to a maximum normal blood clot time for that particular test. Therefore, in this test, the plasma/reagent/liquid crystal mixture is yellow in the abnormally short clot time section of the strip, changes color to red in the normal section of the strip, and then turns yellow again if the blood clot time is too long. The micro-heater gradient could also be reversed so as to at first increase in density up to 22 degrees C., stay above 22 degrees C. in the normal range, and then decrease to below 22 degrees C. if the blood clot time is too long (in this scenario, the patient/doctor would look to the mixture to turn from red (abnormally short) to yellow (normal) to red again (if abnormally long).

Of course, the change of color at 22 degrees C. is just one example. The temperature color change is "selected" by choice, from a broad family of liquid crystal. The temperature "trigger point" could be almost any value. In addition, the color change could be for a short distance along the strip, and then change back to the base color.

Figure 12:
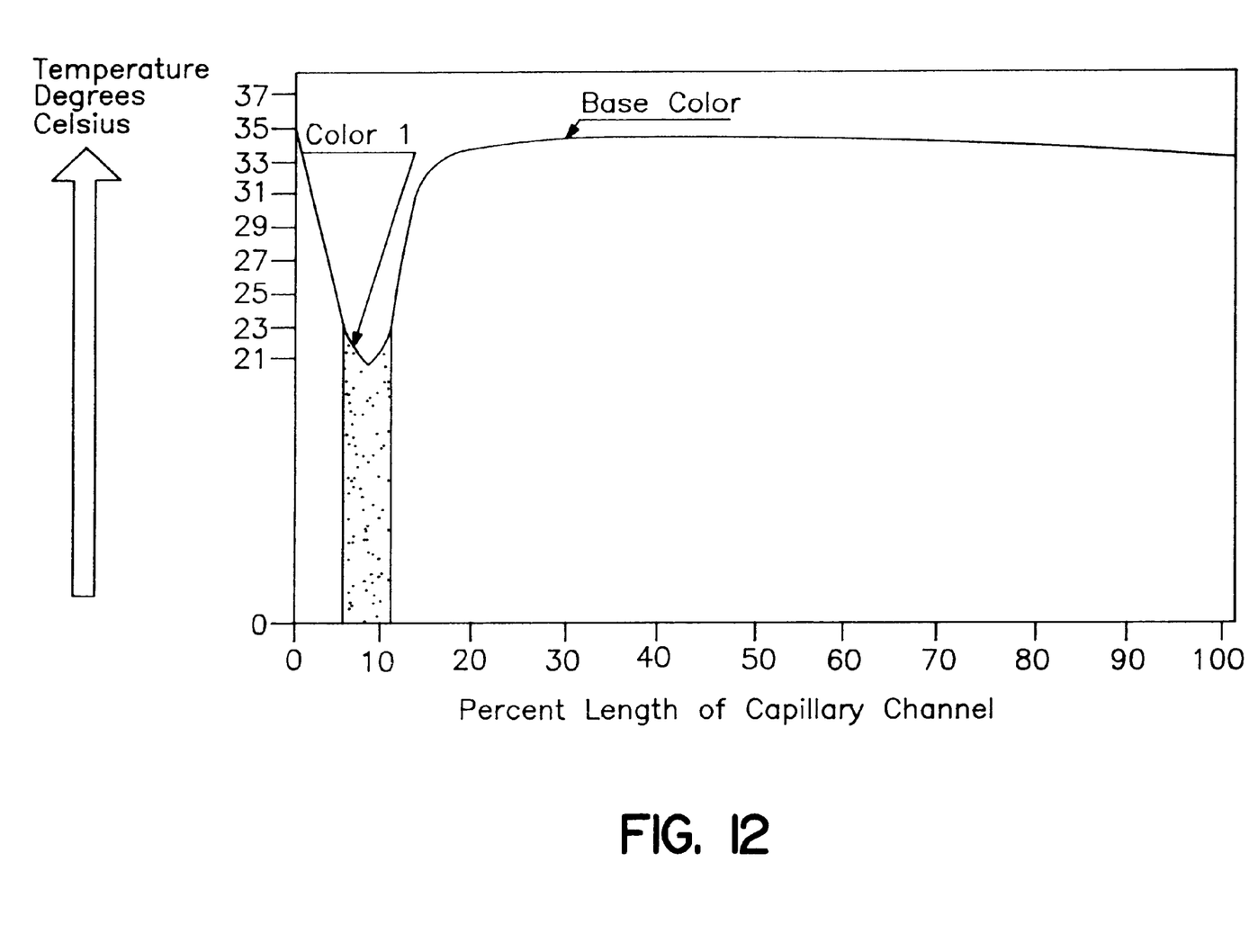
FIG. 12 is a graph showing an additional embodiment of the invention where the base color changes to a second color ("color 1") for a short distance along the capillary channel, and then changes back to base color.
Figure 13:
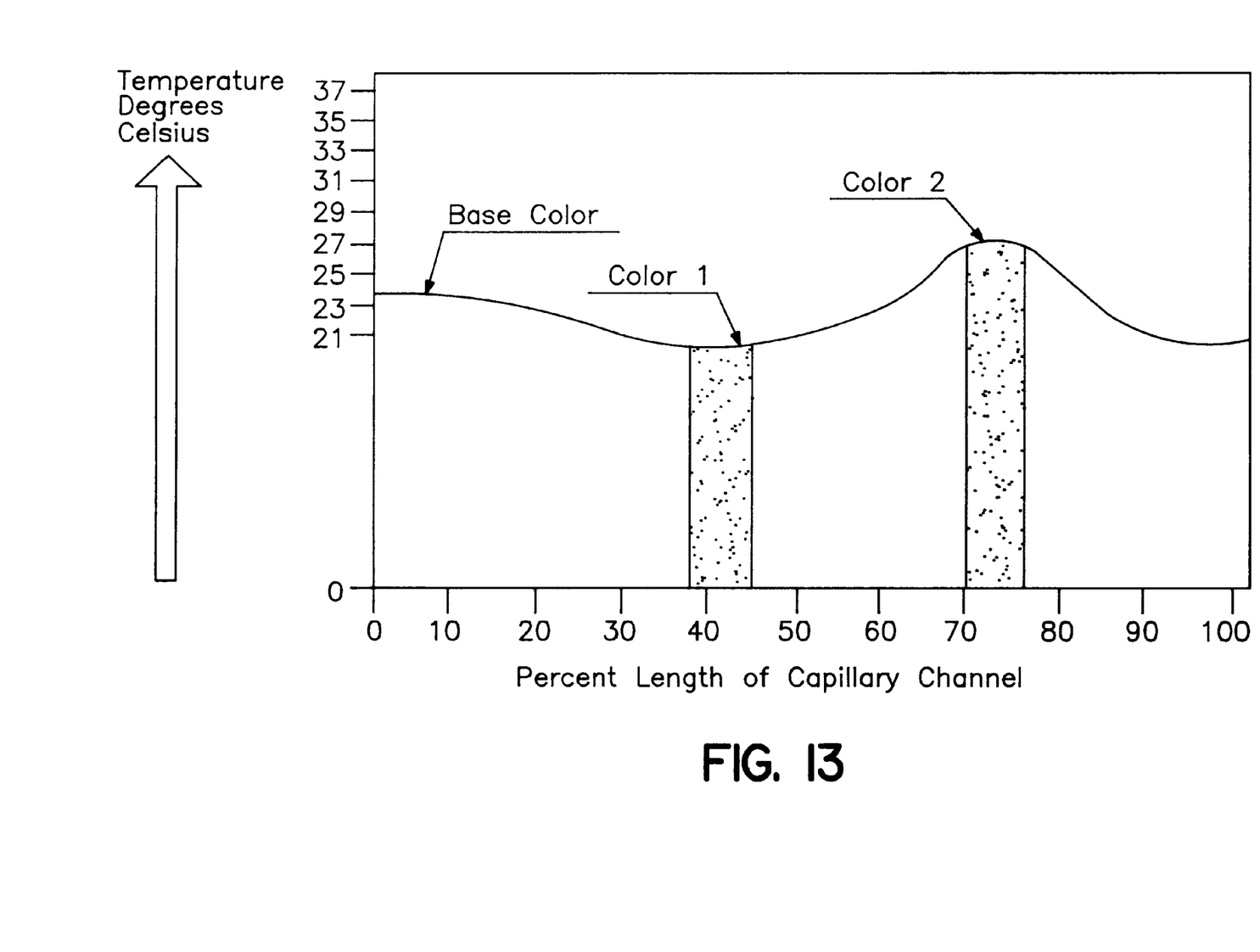
FIG. 13 is a graph showing an additional embodiment of the invention where the base color changes only temporarily to a second color as in FIG. 12, and at a further distance again changes only temporarily to a second color before changing back to base color.

For example, as can be seen in FIG. 12, the device could be designed so as to change color to a second color ("color 1") only for a short distance along the device and then change back again. This would result in a thin color band across the device. As an example in FIG. 12, the change in color is only between 7 to 11 percent of the length of the capillary channel. Such a design could be helpful in diagnosing a very specific coagulation disorder. Likewise, as can be seen in FIG. 13, two different color changes could be incorporated, one when the temperature goes below a particular point, and another when the temperature goes above a particular point. As one example, the first color change could be set at the transition point between abnormally short clot time and normal clot time, whereas the second color change could be set at the transition point between normal clot time and abnormally long clot time. A patient or healthcare worker would look for a single color band (normal), whereas no color band or two bands would indicate an abnormality. In fact, the number and types of combinations of all the examples given above is limitless, depending on what condition is being monitored and what information is desired to be obtained.

As can be seen from the above, an easy to use, disposable device is provided which requires little or no skill to use. The device allows for qualitative detection of coagulation abnormalities within 5 minutes or less. The device is made of inexpensive components, such as a housing made of plastic and a simple thermal gradient with sections wired in series (with the resulting resistive element being controlled in a constant current or voltage mode, and which can be controlled using pulse-modulation techniques). The micro-heater of the invention can use each of its individual heating elements as a temperature sensor and which, by means of manipulating its thermal output, can move fluids along its axis in the capillary channel.

The device also benefits from the use of a simple filter (e.g. a polysulfone membrane) which separates plasma from whole blood components without the need for pressure or vacuum driving forces. The blood separation technique of the present invention presents the opening of a flat capillary channel aligned with the natural gap between the filter material and the sample cavity, and which uses the capillary force of the spatial gap naturally created by contact of the filter material with the sample cavity where it resides.

It will be understood that the above description of the present invention is susceptible to various modifications, changes and adaptations, and the same are intended to be comprehended within the meaning and range of equivalents of the appended claims. As an example, the capillary channel could be replaced by an absorbent material for allowing plasma and liquid crystal to flow along the micro-heater. Likewise, the device could be made part of a vacuum blood collection device, where blood is withdrawn from a patient in a hospital, and within the same apparatus, allowed to mix with liquid crystal and pass into the capillary channel.

Also, besides whole blood, blood components, such as plasma could be used (the term "blood sample" herein includes whole blood as well as blood components such as plasma). If plasma is used, then the membrane adjacent the sample cavity would not be necessary. Also, though the liquid crystal and blood clotting reagent are disclosed as being part of the device, one or both could be mixed with the blood sample before adding the blood sample to the device, in which case they would not need to be contained within the device.

We claim:

1. A device for determining whether or not an individual has a blood coagulation time in a normal range, comprising:
   a housing comprising a blood sample receiving area;
   a capillary channel in fluid communication with said blood sample receiving area;
   a gradient heater disposed along the capillary channel, the gradient heater constructed so as to heat said capillary channel at a varying temperature along the length of the capillary channel and liquid crystal disposed at sample receiving area or between said sample receiving area and said capillary channel, said liquid crystal capable of mixing, at least in part, with a blood sample applied to the device.

2. The device of claim 1, further comprising a reagent chamber disposed between the sample receiving area and said capillary channel, said reagent chamber having said liquid crystal therein.

3. The device of claim 2, wherein said gradient heater is disposed adjacent both said reagent chamber and said capillary channel.

4. The device of claim 1, wherein said gradient heater is constructed so as to heat said capillary channel at a decreasing temperature in a direction away from said sample receiving area.

5. The device of claim 1, wherein said gradient heater is a resistive element having variable density.

6. The device of claim 5, wherein said gradient heater is a plurality of resistive elements, one resistive element having a different density than an adjacent resistive element.

7. The device of claim 1, wherein said liquid crystal changes color at a temperature that is within a temperature gradient along the capillary channel.

8. The device of claim 7, wherein a point along the capillary channel where the liquid crystal changes color is set to correspond to a point where a normal clot time changes to an abnormally long clot time.

9. The device of claim 7, wherein a point along the capillary channel where the liquid crystal changes color is set to correspond to a point where an abnormally short clot time changes to a normal clot time.

10. The device of claim 7, wherein the gradient heater has both increases and decreases of temperature along the capillary channel.

11. The device of claim 10, wherein the liquid crystal is capable of changing color multiple times along the capillary channel.

12. The device of claim 1, comprising more than one type of liquid crystal.

13. The device of claim 1, further comprising an interface port which connects to ends of said gradient heater so as to control voltage or current applied to said gradient heater.

14. The device of claim 1, wherein at said sample receiving area is disposed a sample cavity for receiving a fluid blood sample.

15. The device of claim 14, further comprising a membrane disposed adjacent the sample cavity for filtering out blood components from plasma.

16. A method for determining whether an individual has a blood coagulation time in an abnormal range, comprising:
   a) adding a blood sample from said individual to the device of claim 1;
   b) before or after step a), allowing the blood sample to mix with said liquid crystal and a blood clotting reagent to form a mixture and passing the mixture through said capillary channel;
   c) after the mixture clots within the capillary channel, measuring the furthest distance of travel of the mixture in the capillary channel from said sample receiving area; and
   d) based on the measurement in step c), determining whether the individual has a blood coagulation time in an abnormal range.

17. The method of claim 16, further comprising filtering the blood sample before or after step a) so as to obtain a blood sample comprised predominantly or entirely of plasma, after which the filtered blood sample is mixed with the liquid crystal and blood clotting reagent in step b).

18. The method of claim 16, wherein in step d) the abnormal range is an abnormally short or abnormally long blood coagulation time.

19. The method of claim 16, wherein in step b), the blood sample mixes with the liquid crystal and blood clotting agent in a reagent chamber.

20. The method of claim 19, wherein the reagent chamber comprises two compartments, one compartment having therein the liquid crystal, and the other compartment having therein the blood clotting reagent, said blood sample passing into and mixing with the liquid crystal and blood clotting reagent in each compartment before passing into the capillary channel.

21. The method of claim 16, wherein the blood clotting reagent is thromboplastin or platelin-L.

22. The method of claim 16, wherein in step d), the blood coagulation time is determined to be abnormal based on whether the liquid crystal undergoes a first color change at some point along the capillary channel.

23. The method of claim 22, wherein the blood coagulation time is determined to be normal based on whether the liquid crystal undergoes a second color change.

* * * * *